United States Patent [19]

Clemence et al.

[11] 4,450,166
[45] May 22, 1984

[54] N-(4,5-DIHYDRO-THIAZOL-2-YL)-3-QUINO-LINE-CARBOXAMIDES HAVING ANXIOLYTIC ACTIVITY

[75] Inventors: Francois Clemence, Paris; Peter F. Hunt, Gonesse; Odile Le Martret, Paris; Daniel Humbert, Fontenay Sous Bois, all of France

[73] Assignee: Roussel Uclaf, Paris, France

[21] Appl. No.: 386,597

[22] Filed: Jun. 9, 1982

[30] Foreign Application Priority Data

Jun. 12, 1981 [FR] France .................. 81 11607
Mar. 15, 1982 [FR] France .................. 82 04331

[51] Int. Cl.³ .................... A61K 31/47; C07D 215/56
[52] U.S. Cl. ..................................... 424/258; 546/156
[58] Field of Search ........................ 546/156; 424/258

[56] References Cited

U.S. PATENT DOCUMENTS 3,992,540 11/1976 Clemence et al. ............... 424/258
4,107,310 8/1978 Allais et al. ..................... 424/258
4,299,831 11/1981 Clemence et al. ............... 424/251

FOREIGN PATENT DOCUMENTS 0040573 11/1981 European Pat. Off. ......... 546/156

Primary Examiner—Donald G. Daus
Assistant Examiner—Diana G. Rivers
Attorney, Agent, or Firm—Charles A. Muserlian

[57] ABSTRACT

Novel N-(4,5-dihydro-thiazol-2-yl)-4-hydroxy-3-quinoline-carboxamides of the formula

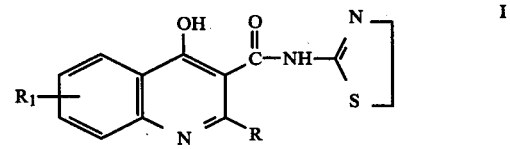

wherein R is selected from the group consisting of hydrogen and alkyl of 1 to 4 carbon atoms and $R_1$ is selected from the group consisting of hydrogen, halogen, linear alkyl of 1 to 4 carbon atoms, branched alkyl of 3 to 5 carbon atoms, alkoxy of 1 to 4 carbon atoms, $CF_3$—, $CF_3O$—, $CF_3S$— and $CH_3S$— in the 6- or 7-position and their non-toxic, pharmaceutically acceptable acid addition salts having a strong anxiolytic activity and a remarkable affinity for benzodiapines receptors and their preparation.

27 Claims, No Drawings

N-(4,5-DIHYDRO-THIAZOL-2-YL)-3-QUINOLINE-CARBOXAMIDES HAVING ANXIOLYTIC ACTIVITY

STATE OF THE ART

Commonly assigned U.S. Pat. No. 3,992,540 describes 4-hydroxy-3-quinoline-carboxamides without a N-(4,5-dihydrothiazol-2-yl) substitution and commonly assigned U.S. Pat. No. 4,107,310 describes 4-hydroxy-3-quinolines with an entirely different physiological activity. French Pat. No. 1,364,605 describes the preparation of quinoline-carboxamides different from those of formula I.

French Pat. No. 2,340,735 describes a large genus of N-substituted 4-hydroxy-3-quinoline-carboxamides with the quinoline ring substituted in the 5-, 6-, 7- or 8-position with diverse substituents. Among the said substituents are mentioned various heterocyclic groups such as thiazolyl or 4,5-dihydrothiazolyl but the only specific derivative described therein for the nitrogen of the amide group is substituted with a 4,5-dihydrothiazolyl group containing an 8-$CF_3$ group of the quinoline which has analgesic activity but is devoid of anxiolytic activity.

OBJECTS OF THE INVENTION

It is an object of the invention to provide the novel N-(4,5-dihydro-thiazol-2-yl)-4-hydroxy-3-quinoline-carboxamides of formula I and their non-toxic, pharmaceutically acceptable acid addition salts and their preparation.

It is another object of the invention to provide a novel method of inducing anxiolytic activity in warm-blooded animals and novel anxiolytic compositions.

These and other objects and advantages of the invention will become obvious from the following detailed description.

THE INVENTION

The novel compounds of the invention are selected from the group consisting of N-(4,5-dihydro-thiazol-2-yl)-4-hydroxy-3-quinoline-carboxamides of the formula

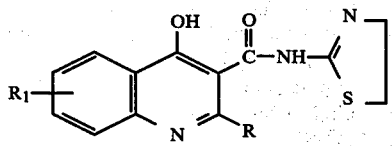

wherein R is selected from the group consisting of hydrogen and alkyl of 1 to 4 carbon atoms and $R_1$ is selected from the group consisting of hydrogen, halogen, linear alkyl of 1 to 4 carbon atoms, branched alkyl of 3 to 5 carbon atoms, alkoxy of 1 to 4 carbon atoms, $CF_3$—, $CF_3O$—, $CF_3S$— and $CH_3S$— in the 6- or 7- position and their non-toxic, pharmaceutically acceptable acid addition salts.

In contrast to the compounds of French Pat. No. 2,340,735, the compounds of formula I are devoid of analgesic activity but possess marked anxiolytic properties as well as a strong affinity for receptors of benzodiazepines.

Examples of R are hydrogen and alkyl such as propyl or isopropyl and preferably methyl and ethyl. Examples of $R_1$ are linear alkyl such as methyl, ethyl and n-propyl, halogens such as fluorine, bromine or chlorine, branched alkyl such as isopropyl or isobutyl, alkoxy such as methoxy, ethoxy or propoxy, $CF_3S$—, $CF_3O$—, $CH_3S$— and $CF_3$—.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as acetic acid, formic acid, propionic acid, maleic acid, benzoic acid, fumaric acid, succinic acid, tartaric acid, citric acid, oxalic acid, glyoxylic acid, aspartic acid, arylsulfonic acids such as benzene sulfonic acid or p-toluene sulfonic acid, alkyl sulfonic acids such as methane sulfonic acid or ethane sulfonic acid and arylcarboxylic acids.

Among the preferred compounds of formula I are those wherein R is hydrogen or methyl, those wherein $R_1$ is hydrogen or chlorine or $CH_3O$— and those wherein $R_1$ is in the 6-position and is fluorine, methyl, ethyl, isopropyl, methylthio or $CF_3$— and their non-toxic, pharmaceutically acceptable acid addition salts. Especially preferred are the compounds of formula I wherein R is hydrogen and most especially N-(4,5-dihydro-thiazol-2-yl)-4-hydroxy-3-quinoline-carboxamide, N-(4,5-dihydro-thiazolyl-2-yl)-6-ethyl-4-hydroxy-3-quinoline-carboxamide, N-(4,5-dihydro-thiazol-2-yl)-6-chloro-4-hydroxy-3-quinoline-carboxamide, N-(4,5-dihydro-thiazol-2-yl)-2-methyl-4-hydroxy-3-quinoline carboxamide and their non-toxic, pharmaceutically acceptable acid addition salts.

The novel proces of the invention for the preparation of the compounds of formula I comprises reacting a compound of the formula

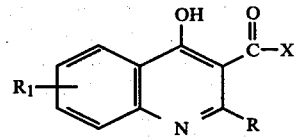

wherein R and $R_1$ have the above definitions and X is selected from the group consisting of chlorine, bromine, and —OH and alkoxy of 1 to 5 carbon atoms with 2-amino-thiazoline to obtain the corresponding compound of formula I, which may be salified, if desired.

The reaction of the acid chloride or acid bromide of formula II with 2-amino-thiazoline is preferably effected in a solvent or an inert suspension in lower aliphatic ketones, dioxane, dimethylformamide, benzene, toluene or alkyl halides, preferably in the presence of an acceptor for hydroacids such as potassium hydroxide, alkali metal carbonates such as potassium carbonate, alkali metal bicarbonates such as sodium bicarbonate and potassium bicarbonate, alkali metal alcoholates such as sodium ethylate or preferably tertiary amines such as trialkylamines or pyridine.

The reaction of an acid of formula II with 2-amino-thiazoline is preferably effected in the presence of dicyclohexylcarbodiimide in dimethylformaide.

Preferably, the alkyl esters of formula II, especially the ethyl ester, is reacted at reflux in one of the solvents discussed above having a boiling point of 50° to 150° C., and the reflux is preferably maintained for 12 to 48 hours. The reaction is preferably effected in the presence of a condensation agent such as alkyl derivatives of aluminum such as trimethylaluminum and especially triisobutylaluminum or in the presence of traces of an alkali metal hydride such as sodium hydride.

The compounds of formula II are known and are prepared by the process described in French Pat. No. 2,340,735.

Because of the basic character of the compounds of formula I, the acid addition salts thereof are easily prepared by reacting approximately stoichometric amounts of the compound of formula I and an inorganic or organic acid and the salts may be prepared without isolation of the free base.

The novel anxiolytic compositions of the invention are comprised of an anxiolytically effective amount of at least one compound of formula I and their non-toxic, pharmaceutically acceptable acid addition salts and inert pharmaceutical carrier or excipient. The compositions may be in the form of tablets, dragees, gelules, granules, suppositories or injectable solutions or suspensions.

Examples of suitable excipients are talc, arabic gum, lactose, starch, magnesium stearate, cocao butter, aqueous or non-aqueous vehicles, fatty bodies of animal or vegetable origin, paraffinic derivatives, glycols, diverse wetting agents, dispersants or emulsifiers and preservatives.

The compositions due to their strong anxiolytic activity are useful for the treatment of anxiety states such as chronic anxiety associated or not with insomnia or behavior problems, anguish in adults or children or as a complement to treatment with neuroleptics or antidepressants of psychotic or depressive states.

Among the preferred compositions are those wherein R is hydrogen or methyl, those wherein $R_1$ is hydrogen or chlorine or $CH_3O-$ and those wherein $R_1$ is in the 6-position and is fluorine, methyl, ethyl, isopropyl, methylthio or $CF_3-$ and their non-toxic, pharmaceutically acceptable acid addition salts. Especially preferred are the compounds of formula I wherein R is hydrogen and most especially N-(4,5-dihydro-thiazol-2-yl)-4-hydroxy-3-quinoline-carboxamide, N-(4,5-dihydro-thiazol-2-yl)-6-ethyl-4-hydroxy-3-quinoline-carboxamide, N-(4,5-dihydro-thiazol-2-yl)-6-chloro-4-hydroxy-3-quinoline-carboxamide, N-(4,5-dihydro-thiazol-2-yl)-2-methyl-4-hydroxy-3-quinoline-carboxamide and their non-toxic, pharmaceutically acceptable acid addition salts.

The novel method of the invention of inducing anxiolytic activity in warm-blooded animals, including humans, comprises administering to warm-blooded animals an anxiolytically effective amount of at least one compound of formula I and their non-toxic, pharmaceutically acceptable acid addition salts. The compounds may be administered orally, rectally or parenterally and the usual effective dose will vary depending on the condition being treated or the specific compound. The usual daily dose is 0.015 to 1.5 mg/kg administered orally in man, with the compound of example 1.

In the following examples there are described several preferred embodiments to illustrate the invention. However, it is to be understood that the invention is not intended to be limited to the specific embodiments.

EXAMPLE 1

N-(4,5-dihydro-thiazol-2-yl)-4-hydroxy-3-quinoline-carboxamide hydrochloride 167 ml of a solution of 25% by weight of triisobutyl aluminum in toluene were added with stirring over 20 minutes at 8° to 10° C. to a mixture of 37.4 g of 2-amino-thiazoline and 800 ml of methylene chloride and the mixture was stirred at 8° C. for 30 minutes. 15.89 g of 3-carbethoxy-4-hydroxy-quinoline were added to the mixture which was then stirred for 30 minutes and then refluxed for 16 hours. The mixture was evaporated to dryness under reduced pressure and the residue was taken up in 1 liter of N aqueous hydrochloric acid. The solution was filtered and the filtrate was iced for 16 hours and was filtered. The product was washed with water and the filtrate was made alkaline with sodium carbonate. The mixture was filtered and the product was washed with water and dried to obtain 11.7 g of N-(4,5-dihydro-thiazol-2-yl)-4-hydroxy-3-quinoline-carboxamide.

The product was dissolved in 600 ml of ethanol and the solution was filtered. 8 ml of ethanolic 5.3 N hydrochloric acid were added to the filtrate and the mixture was iced and filtered. The product was dried to obtain 8.5 g of N-(4,5-dihydro-thiazol-2-yl)-4-hydroxy-3-quinoline-carboxamide hydrochloride melting at ≃300° C.

Analysis: $C_{13}H_{11}N_3O_2S.HCl$; molecular weight=309.78. Calculated: %C 50.41; %H 3.9; %N 13.56; %S 10.35; %Cl 11.44. Found: %C 50.1; %H 4.0; %N 13.3; %S 10.4; %Cl 11.2.

EXAMPLE 2

N-(4,5-dihydro-thiazol-2-yl)-6-ethyl-4-hydroxy-quinoline-carboxamide hydrochloride STEP A: Ethyl 4-ethylphenylaminomethylenepropanedioate A mixture of 50 g of 4-ethyl-aniline and 89 g of ethyl ethoxymethylenemalonate was refluxed at 160° C. with stirring under an inert atmosphere while distilling the ethanol formed and the mixture was cooled to form ethyl 4-ethylphenylaminomethylenepropanedioate in the form of an oil which was used as is for the next step.

STEP B: Ethyl 4-hydroxy-6-ethyl-3-quinoline-carboxylate

A mixture of the oil of Step A and 70 ml of phenyl oxide was stirred under an inert atmosphere and was then heated at 250° C. for one hour while distilling the formed ethanol. The mixture was cooled and 30 ml of acetone were added thereto. The mixture was vacuum filtered and the product was empasted with 30 ml of acetone and was dried and crystallized from ethanol to obtain 36 g of ethyl 4-hydroxy-6-ethyl-3-quinoline-carboxylate melting at >260° C.

Analysis: $C_{14}H_{15}NO_3$; molecular weight=245.28. Calculated: %C 68.55; %H 6.16; %N 5.71. Found: %C 68.6; %H 6.1; %N 5.7.

STEP C: N-(4,5-dihydro-thiazol-2-yl)-6-ethyl-4-hydroxy-3-quinoline-carboxamide hydrochloride 45.36 ml of 1.1 M of triisobutyl aluminum in toluene were added with stirring over 10 minutes at 7° to 10° C. to a mixture of 10.2 g of 2-amino-thiazoline and 500 ml of methylene chloride and the mixture was stirred at 7° to 10° C. for one hour. 4.88 of ethyl 6-ethyl-4-hydroxy-3-quinolin-carboxamide were added to the mixture which was then refluxed for 16 hours. The mixture was evaporated to dryness under reduced pressure and the residue was taken up to 100 ml of aqueous N hydrochloric acid solution. The solution was heated at 70° C. for 2 hours and was treated with activated carbon and filtered. The filtrate was allowed to crystallize and was then vacuum filtered. The recovered product was washed with aqueous N hydrochloric acid solution and was dried under reduced pressure and crystallized from acetic acid to obtain 2.2 g of N-(4,5-dihydro-thiazol-2-yl)-6-ethyl-4-hydroxy-3-quinoline-carboxamide hydrochloride melting at >260° C.

Analysis: $C_{15}H_{16}N_3O_2S.HCl$; molecular weight=337.83. Calculated: %C 53.33; %H 4.77; %N 12.44; %S 9.49; %Cl 10.49. Found: %C 53.1; %H 4.7; %N 12.3; %S 9.5; %Cl 10.3.

EXAMPLE 3

STEP A: Ethyl 6-methyl-4-hydroxy-3-quinoline-carboxylate

Using the procedure of Example 2, ethyl ethoxymethylene malonate and 4-methyl-aniline were reacted and treated with phenyl oxide to obtain ethyl 6-methyl-4-hydroxy-3-quinoline-carboxylate melting at >260° C.

Analysis: $C_{13}H_{13}NO_3$; molecular weight=231.24. Calculated: %C 67.52; %H 5.69; %N 6.05. Found: %C 67.2; %H 5.7; %N 6.0.

STEP B: N-(4,5-dihydro-thiazol-2-yl)-6-methyl-4-hydroxy-3-quinoline-carboxamide hydrochloride Using the procedure of Example 2, ethyl 6-methyl-4-hydroxy-3-quinoline-carboxylate and 2-amino-thiazoline were reacted at reflux for 48 hours and the product was crystallized from acetic acid to obtain N-(4,5-dihydro-thiazol-2-yl)-6-methyl-4-hydroxy-3-quinoline-carboxamide hydrochloride at >260° C.

Analysis: $C_{14}H_{14}ClN_3O_2S$; molecular weight=323.803. Calculated: %C 51.93; %H 4.35; %N 12.97; %S 9.90; %Cl 10.94. Found: %C 51.6; %H 4.5; %N 12.9; %S 9.7; %Cl 10.9.

EXAMPLE 4

Using the procedure of Example 2, ethyl 6-isopropyl-4-hydroxy-3-quinoline-carboxylate and 2-amino-thiazoline were reacted at reflux for 48 hours and the product was crystallized from acetic acid to obtain N-(4,5-dihydro-thiazol-2-yl)-6-isopropyl-4-hydroxy-3-quinoline-carboxamide hydrochloride melting at >260° C.

Analysis: $C_{16}H_{18}ClN_3O_2S$; molcular weight=351.85. Calculated: %C 54.62; %H 5.15; %N 11.94; %S 9.11; %Cl 10.07. Found: %C 54.6; %H 5.1; %N 11.7; %S 9.0; %Cl 10.4.

EXAMPLE 5

Using the procedure of Example 2, ethyl 7-chloro-4-hydroxy-3-quinoline-carboxylate and 2-amino-thiazoline were reacted at reflux for 48 hours and the product was crystallized from acetic acid to obtain N-(4,5-dihydro-thiazol-2-yl)-7-chloro-4-hydroxy-3-quinoline-carboxamide hydrochloride melting at >260° C.

Analysis: $C_{13}H_{11}Cl_2N_3O_2S$; molecular weight=344.22. Calculated: %C 45.36; %H 3.22; %N 12.20; %S 9.31; %Cl 20.60. Found: %C 45.2; %H 3.3; %N 12.3; %S 9.0; %Cl 20.6.

EXAMPLE 6

STEP A: Ethyl 6-chloro-4-hydroxy-3-quinoline-carboxylate

Using the procedure of Example 2, ethyl ethoxymethylene malonate and 4-chloro-aniline were reacted and treated with phenyl oxide to obtain ethyl 6-chloro-4-hydroxy-3-quinoline-carboxylate melting at >260° C.

Analysis: $C_{12}H_{10}ClNO_3$; molecular weight=251.7. Calculated: %C 57.27; %H 4.00; %N 5.56; %Cl 14.08. Found: %C 57.5; %H 4.0; %N 5.5; %Cl 14.0.

STEP B: N-(4,5-dihydro-thiazol-2-yl)-6-chloro-4-hydroxy-3-quinoline-carboxamide hydrochloride Using the procedure of Example 2, ethyl 6-chloro-4-hydroxy-3-quinoline-carboxylate and 2-amino-thiazoline were reacted at reflux for 48 hours and the product was crystallized from acetic acid to obtain N-(4,5-dihydro-thiazol-2-yl)-6-chloro-4-hydroxy-3-quinoline-carboxamide hydrochloride melting at >260° C.

Analysis: $C_{13}H_{11}Cl_2N_3O_2S$; molecular weight=344.22. Calculated: %C 45.36; %H 3.22; %N 12.20; %S 9.31; %Cl 20.60. Found: %C 45.1; %H 3.3; %N 12.3; %S 9.5; %Cl 20.3.

EXAMPLE 7

STEP A: Ethyl 6-fluoro-4-hydroxy-3-quinoline-carboxylate

Using the procedure of Example 2, ethyl ethoxymethylene malonate and 4-fluoro-aniline were reacted and treated with phenyl oxide to obtain ethyl 6-fluoro-4-hydroxy-3-quinoline-carboxylate melting at >260° C.

Analysis: $C_{12}H_{10}FNO_3$; molecular weight=234.22. Calculated: %C 61.53; %H 4.30; %N 5.93; %F 8.11. Found: %C 61.3; %H 4.3; %N 6.0; %F 8.0.

STEP B: N-(4,5-dihydro-thiazol-2-yl)-6-fluoro-4-hydroxy-3-quinoline-carboxamide hydrochloride Using the procedure of Example 2, ethyl 6-fluoro-4-hydroxy-3-quinoline-carboxylate and 2-amino-thiazoline were reacted at reflux for 48 hours and the product was crystallized from acetic acid to obtain N-(4,5-dihydro-thiazol-2-yl)-6-fluoro-4-hydroxy-3-quinoline-carboxamide hydrochloride melting at >260° C.

Analysis: $C_{13}H_{11}ClFN_3O_2S$; molecular weight=327.76. Calculated: %C 47.64; %H 3.38; %N 12.82; %S 9.78; %Cl 10.81; %F 5.79. Found: %C 47.4; %H 3.4; %N 12.7; %S 9.7; %Cl 10.4; %F 5.9.

EXAMPLE 8

STEP A: Ethyl 7-methoxy-4-hydroxy-3-quinoline-carboxylate

Using the procedure of Example 2, ethyl ethoxymethylene malonate and 3-methoxy-aniline were reacted and treated with phenyl oxide to obtain ethyl 7-methoxy-4-hydroxy-3-quinoline-carboxylate melting at >260° C.

Analysis: $C_{13}H_{13}NO_4$; molecular weight=247.31. Calculated: %C 63.15; %H 5.3; %N 5.66. Found: %C 63.1; %H 5.4; %N 5.7.

STEP B: N-(4,5-dihydro-thiazol-2-yl)-7-methoxy-4-hydroxy-3-quinoline-carboxamide hydrochloride Using the procedure of Example 2, ethyl 7-methoxy-4-hydroxy-3-quinoline-carboxylate and 2-amino-thiazoline were reacted at reflux for 48 hours and the product was crystallized from acetic acid to obtain N-(4,5-dihydro-thiazol-2-yl)-7-methoxy-4-hydroxy-3-quinoline-carboxamide hydrochloride melting at >260° C.

Analysis: $C_{14}H_{14}ClN_3O_3S$; molecular weight 339.79. Calculated: %C 49.50; %H 4.15; %N 12.36; %S 9.43; %Cl 10.43. Found: %C 49.8; %H 4.1; %N 12.2; %S 9.2; %Cl 10.1.

EXAMPLE 9

Using the procedure of Example 2, ethyl 2-methyl-4-hydroxy-3-quinoline-carboxylate and 2-amino-thiazoline were reacted at reflux for 48 hours and the product was crystallized from acetic acid to obtain N-(4,5-dihydro-thiazol-2-yl)-2-methyl-4-hydroxy-3-quinoline-carboxamide hydrochloride melting at 280° C. with decomposition.

Analysis: $C_{14}H_{14}ClN_3O_2S$; molecular weight=323.803. Calculated: %C 51.92; %H 4.36; %N 12.97; %S 9.90; %Cl 10.95. Found: %C 52.2; %H 4.5; %N 13.3; %S 9.9; %Cl 10.6.

EXAMPLE 10

STEP A: Ethyl 6-methylthio-4-hydroxy-3-quinoline-carboxylate

Using the procedure of Example 2, ethyl ethoxymethylene malonate and 4-methylthio-aniline were reacted and treated with phenyl oxide to obtain ethyl 6-methylthio-4-hydroxy-3-quinoline-carboxylate melting at >260° C.

Analysis: $C_{13}H_{13}NO_3S$; molecular weight=263.31. Calculated: %C 59.3; %H 4.97; %N 5.32; %S 12.17. Found: %C 59.0; %H 5.0; %N 5.4; %S 12.3.

STEP B: N-(4,5-dihydro-thiazol-2-yl)-6-methylthio-4-hydroxy-3-quinoline-carboxamide hydrochloride Using the procedure of Example 2, ethyl 6-methylthio-4-hydroxy-3-quinoline-carboxylate and 2-amino-thiazoline were reacted at reflux for 48 hours and the product was crystallized from acetic acid to obtain N-(4,5-dihydro-thiazol-2-yl)-6-methylthio-4-hydroxy-3-quinoline-carboxamide hydrochloride melting at >260° C.

Analysis: $C_{14}H_{14}ClN_3O_2S_2$; molecular weight=355.80. Calculated: %C 47.26; %H 3.96; %N 11.81; %S 18.02; %Cl 9.96. Found: %C 47.2; %H 4.0; %N 11.5; %S 17.8; %Cl 9.7.

EXAMPLE 11

STEP A: Ethyl 6-trifluoromethyl-4-hydroxy-3-quinoline-carboxylate

Using the procedure of Example 2, ethyl ethoxymethylene malonate and 4-trifluoromethyl-aniline were reacted and treated with phenyl oxide to obtain ethyl 6-trifluoromethyl-4-hydroxy-3-quinoline-carboxylate melting at >260° C.

Analysis: $C_{13}H_{10}NO_3F_3$; molecular weight=285.00 Calculated: %C 54.78; %H 3.53; %N 4.91; %F 19.99. Found: %C 54.5; %H 3.5; %N 4.9; %F 20.2.

STEP B: N-(4,5-dihydro-thiazol-2-yl)-6-trifluoromethyl-4-hydroxy-3-quinoline-carboxamide hydrochloride Using the procedure of Example 2, ethyl 6-trifluoromethyl-4-hydroxy-3-quinoline-carboxylate and 2-amino-thiazoline were reacted at reflux for 48 hours and the product was crystallized from acetic acid to obtain N-(4,5-dihydro-thiazol-2-yl)-6-trifluoromethyl-4-hydroxy-3-quinoline-carboxamide hydrochloride melting at >260° C.

Analysis: $C_{14}H_{11}ClF_3N_3O_2S$; molecular weight=377.77. Calculated: %C 44.51; %H 2.93; %N 11.12; %S 8.48; %Cl 9.38; %F 15.08. Found: %C 44.3; %H 2.9; %N 11.1; %S 8.7; %Cl 9.4; %F 15.3.

EXAMPLE 12

STEP A: Ethyl 6-methoxy-4-hydroxy-3-quinoline-carboxylate

Using the procedure of Example 2, ethyl ethoxymethylene malonate and 4-methoxy-aniline were reacted and treated with phenyl oxide to obtain ethyl 6-methoxy-4-hydroxy-3-quinoline-carboxylate melting at >260° C.

Analysis: $C_{13}H_{13}NO_4$; molecular weight=247.31. Calculated: %C 63.15; %H 5.3; %N 5.66. Found: %C 63.1; %H 5.4; %N 5.7.

STEP B: N-(4,5-dihydro-thiazol-2-yl)-6-methoxy-4-hydroxy-3-quinoline-carboxamide hydrochloride Using the procedure of Example 2, ethyl 6-methoxy-4-hydroxy-3-quinoline carboxylate and 2-amino-thiazoline were reacted at reflux for 48 hours and the product was crystallized from acetic acid to obtain N-(4,5-dihydro-thiazol-2-yl)-6-methoxy-4-hydroxy-3-quinoline-carboxamide hydrochloride melting at >260° C.

Analysis: $C_{14}H_{14}ClN_3O_3S$; molecular weight=339.77. Calculated: %C 49.49; %H 4.15; %N 12.36; %S 9.43; %Cl 10.43. Found: %C 49.5; %H 4.1; %N 12.3; %S 9.4; %Cl 10.7.

EXAMPLE 13

Tablets were prepared containing 5 mg of either N-(4,5-dihydro-thiazol-2-yl)-4-hydroxy-3-quinoline-carboxamide hydrochloride or N-(4,5-dihydro-thiazol-2-yl)-6-ethyl-4-hydroxy-3-quinoline-carboxamide hydrochloride or 10 mg of N-(4,5-dihydro-thiazol-2-yl)-6-chloro-4-hydroxy-3-quinoline-carboxamide hydrochloride and sufficient excipient of lactose, starch, talc and magnesium stearate for a final tablet weight of 100 mg.

PHARMACOLOGICAL STUDY

A. Affinity for receptors for benzodiazepines

The test was inspired by Mohler et al. [Science, No. 198 (1977), p. 849–851] and one part of the cortex removed from the brains of males rats weighing an average of 150 mg per 20 parts by volume of 0.32 M of sucrose solution was homogenized. After centrifugation at 1000 g of the homogenized mixture at 0° C. for 10 minutes, the surnagent was centrifuged at 30,000 g at 4° C. for 20 minutes and the culot was suspended in 20 volumes of buffered 50 mM. Tris HCl with a pH of 7.4. The suspension was centrifuged at 30,000 g for 20 minutes at 4° C. and the new culot was suspended in 50 ml of buffered Krebs Tris HCl with a pH of 7.4. Following incubation at 0° C. for 30 minutes, 2 ml of the suspension in the presence of $^3H$ diazepam at a concentration of $10^{-9}M$ alone and with increasing concentrations of the test product to determine non-specific fixation with non-radioactive diazepam at a concentration of $10^{-6}M$.

The incubated suspension were filtered through a Whatman GF/C filter and the filters were washed twice at 0° C. with 5 ml of buffered krebs. Tris HCl with a pH of 7.4. The radioactivity of the filter was measured by liquid scintillation and the activity of the product was expressed in I.C.$_{50}$ or the concentration which inhibits by 50% the specific bonding of $^3H$ diazepam determined graphically. The results are reported in Table I.

TABLE I

| Compound of Example | IC$_{50}$ in nM |
|---|---|
| 1 | 0.5 |
| 2 | 0.3 |
| 3 | 1.5 |
| 4 | 2.2 |
| 5 | 0.9 |
| 6 | 1.0 |
| 7 | 1.3 |
| 8 | 1.2 |
| 9 | 2.6 |

B. Anxiolytic activity

The Apelab apparatus and protocol used by Boissier et al [European J. Pharmacol., Vol. 4 (1968), p. 145] were used to determine the anxiolytic activity and 4 plates were connected to a stimulator (U. Sachs, Roucaire) which delivered electric shocks of 120 volts for 0.5 seconds. The test was effected on groups of 10 mice who had orally received the test compound 30 minutes before the test. Each animal was individually placed on the apparatus and after 15 seconds of free exploration, it was subjected to an electric shock each time as it passed from plate to another, a minimum of 3 seconds being observed between 2 shocks. The number of delivered shocks was determined over one minute and the obtained results were compared to those observed on control animals by the Dunnett test. Table II reports the oral dose at which the number of delivered shocks increased to the maximum.

TABLE II

| Product of Example | Dose in mg/kg |
|---|---|
| 1 | 10 |
| 2 | 20 |
| 4 | 20 |
| 6 | 50 |
| 8 | 20 |
| 9 | 10 |

The products of examples 1,2,4,6,8 and 9 show therefore, good anxoilytic activity.

C. Action against stress caused by noise by plasmatic corticosterone level

The test was effected on groups of 5 rats fasted for 24 hours receiving orally the test compound between 8 and 9 in the morning. One hour later, stress was applied to the animals by placing them in a cage with a noisily operated radio adjacent thereto. 30 minutes later, they received an intraperitonal prick and 10 minutes later, the animals were anesthesized with halothane. 3 ml blood samples were taken after decapitation and the seric levels of corticosterone were determined by a radio-immunological method. Counts were taken of the importance in the male rat of seric concentrations of corticosterone to determine directly without previous extraction of the hormone with 0.1 ml of the sample diluted to 1 to 100. To the test sample were added in hemolysis tubes (12×65 mm) 0.1 ml of an aqueous solution of $^3H$— corticosterone (5000 spm) and 0.5 ml of buffered phosphate solution (0.02 M; pH of 6.9) containing 0.02% of gelatine and 0.02% of sodium nitride containing a suspension of anticorticosterone antiserum (dilution 1/300,000), sheep antiserum anti $\gamma$-globuline of rabbit (dilution of 1/50) and normal serum of rabbit treated with Dextran carbon (dilution 1/500).

The volume was adjusted to 1 ml and the mixture was incubated overnight at 4° C. The mixture was centrifuged at 3000 t/mn for 20 minutes and the surnageant was discarded. The radioactivity contained in the precipitate was measured by a counter after addition of 2 ml of scintillation liquid containing 5% of Soluene 350. The concentration of corticosterone was determined with a standard curve (0–4000 pg) established under the treatment conditions of the samples. The individual seric level of corticosterone expressed in $\mu g/100$ ml was determined as the average of 3 tests and the results were compared by the Student test to those obtained in control animals not subjected to stress. The results expressed as $DE_{50}$ on the oral dose which reduced by 50% the level of corticosterone in the treated animals is reported in Table III.

TABLE III

| Product of Example | $DE_{50}$ in mg/kg |
|---|---|
| 1 | 10 |
| 2 | 15 |
| 4 | 50 |
| 6 | 50 |
| 9 | 10 |

The stress was considerably less in the treated animals and the animals showed a degree of anxiety less than the controls.

D. Acute toxicity

The $DL_0$ lethal dose which is the maximum dose which did not cause any mortality after 8 days was determined orally on mice and the results are reported in Table IV.

TABLE IV

| Compound of Example | $DL_0$ in mg/kg |
|---|---|
| 1 | >400 |
| 2 | >400 |
| 4 | >1000 |
| 5 | >1000 |
| 6 | >400 |
| 8 | >400 |
| 9 | >1000 |

Various modifications of the products and processes of the invention may be made without departing from the spirit or scope thereof and it is to be understood that the invention is intended to be limited only as defined in the appended claims.

What we claim is:

1. A compound selected from the group consisting of N-(4,5-dihydro-thiazol-2-yl)-4-hydroxy-3-quinoline-carboxamides of the formula

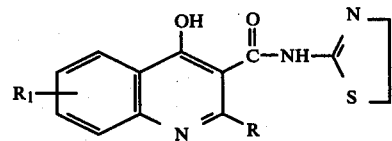

wherein R is selected from the group consisting of hydrogen and alkyl of 1 to 4 carbon atoms and $R_1$ is selected from the group consisting of hydrogen, halogen, linear alkyl of 1 to 4 carbon atoms, branched alkyl of 3 to 5 carbon atoms, alkoxy of 1 to 4 carbon atoms, $CF_3$—, $CF_3O$—, $CF_3S$— and $CH_3S$— in the 6- or 7-position and their non-toxic, pharmaceutically acceptable acid addition salts.

2. A compound of claim 1 wherein R is hydrogen or methyl.

3. A compound of claim 1 or 2 wherein $R_1$ is chlorine or methoxy.

4. A compound of claim 1 or 2 wherein $R_1$ is the 6-position and is selected from the group consisting of fluorine, methyl, ethyl, isopropyl, methylthio and $CF_3$—.

5. A compound of claim 2 wherein R is hydrogen.

6. A compound of claim 1 selected from the group consisting of N-(4,5-dihydro-thiazol-2-yl)-4-hydroxy-3-quinoline-carboxamide and its non-toxic, pharmaceutically acceptable acid addition salts.

7. A compound of claim 1 selected from the group consisting of N-(4,5-dihydro-thiazol-2-yl)-6-ethyl-4- hydroxy-3-quinoline-carboxamide and its non-toxic, pharmaceutically acceptable acid addition salts.

8. A compound of claim 1 selected from the group consisting of N-(4,5-dihydro-thiazol-2-yl)-6-chloro-4-hydroxy-3-quinoline-carboxamide and its non-toxic, pharmaceutically acceptable acid addition salts.

9. A compound of claim 1 selected from the group consisting of N-(4,5-dihydro-thiazol-2-yl)-2-methyl-4-hydroxy-3-quinoline-carboxamide and its non-toxic, pharmaceutically acceptable acid addition salts.

10. An anxiolytic composition comprising an anxiolytically effective amount of at least one compound of claim 1 and a pharmaceutical carrier.

11. A composition of claim 10 wherein R is hydrogen or methyl.

12. A composition of claim 10 wherein $R_1$ is chlorine or methoxy.

13. A composition of claim 10 wherein $R_1$ is in the 6-position and is selected from the group consisting of fluorine, methyl, ethyl, isopropyl, methylthio and $CF_3$—.

14. A composition of claim 10 wherein R is hydrogen.

15. A composition of claim 10 wherein the active compound is selected from the group consisting of N-(4,5-dihydro-thiazol-2-yl)-4-hydroxy-3-quinoline-carboxamide and its non-toxic, pharmaceutically acceptable acid addition salts.

16. A composition of claim 10 wherein the active compound is selected from the group consisting of N-(4,5-dihydro-thiazol-2-yl)-6-ethyl-4-hydroxy-3-quinoline-carboxamide and its non-toxic, pharmaceutically acceptable acid addition salts.

17. A composition of claim 10 wherein the active compound is selected from the group consisting of N-(4,5-dihydro-thiazol-2-yl)-6-chloro-4-hydroxy-3-quinoline-carboxamide and its non-toxic, pharmaceutically acceptable acid addition salts.

18. A composition of claim 10 wherein the active compound is selected from the group consisting of N-(4,5-dihydro-thiazol-2-yl)-2-methyl-4-hydroxy-3-quinoline-carboxamide and its non-toxic, pharmaceutically acceptable acid addition salts.

19. A method of inducing anxiolytic activity in warm-blooded animals comprising administering to warm-blooded animals an anxiolytically effective amount of at least one compound of claim 1.

20. A method of claim 19 wherein R is hydrogen or methyl.

21. A method of claim 19 wherein $R_1$ is chlorine or methoxy.

22. A method of claim 19 wherein $R_1$ is in the 6-position and is selected from the group consisting of fluorine, methyl, ethyl, isopropyl, methylthio and $CF_3$—.

23. A method of claim 19 wherein R is hydrogen.

24. A method of claim 19 wherein the active compound is selected from the group consisting of N-(4,5-dihydro-thiazol-2-yl)-4-hydroxy-3-quinoline-carboxamide and its non-toxic, pharmaceutically acceptable acid addition salts.

25. A method of claim 19 wherein the active compound is selected from the group consisting of N-(4,5-dihydro-thiazol-2-yl)-6-ethyl-4-hydroxy-3-quinoline-carboxamide and its non-toxic, pharmaceutically acceptable acid addition salts.

26. A method of claim 19 wherein the active compound is selected from the group consisting of N-(4,5-dihydro-thiazol-2-yl)-6-chloro-4-hydroxy-3-quinoline-carboxamide and its non-toxic, pharmaceutically acceptable acid addition salts.

27. A method of claim 19 wherein the active compound is selected from the group consisting of N-(4,5-dihydro-thiazol-2-yl)-2-methyl-4-hydroxy-3-quinoline-carboxamide and its non-toxic, pharmaceutically acceptable acid addition salts.

* * * * *